(12) United States Patent
Inaba et al.

(10) Patent No.: US 6,512,147 B2
(45) Date of Patent: Jan. 28, 2003

(54) APPARATUS AND PROCESS FOR GENERATING MIXED MULTI-COMPONENT VAPOR

(75) Inventors: Yukio Inaba, Ube (JP); Kazunori Fujita, Ube (JP); Hiroshi Kofuji, Ube (JP)

(73) Assignee: UBE Industries, Ltd., Ube (JP)

( * ) Notice: Subject to any disclaimer, the term of this patent is extended or adjusted under 35 U.S.C. 154(b) by 0 days.

(21) Appl. No.: 10/108,675

(22) Filed: Mar. 28, 2002

(65) Prior Publication Data

US 2002/0134517 A1 Sep. 26, 2002

Related U.S. Application Data

(62) Division of application No. 09/178,732, filed on Oct. 26, 1998.

(30) Foreign Application Priority Data

Oct. 28, 1997 (JP) ............................................. 9-295757
Oct. 28, 1997 (JP) ............................................. 9-295758

(51) Int. Cl.[7] .......................... C07C 43/23; C07C 41/09
(52) U.S. Cl. ....................... 568/650; 568/651; 568/652; 568/653; 568/648; 568/628
(58) Field of Search ................................ 568/650, 651, 568/652, 653, 648, 628

(56) References Cited

U.S. PATENT DOCUMENTS

| | | | |
|---|---|---|---|
| 3,678,983 A | 7/1972 | Widmer et al. ............... 159/6.2 |
| 4,317,926 A | 3/1982 | Sato et al. ................... 562/532 |
| 4,810,327 A | * 3/1989 | Norrmen .................... 159/13.3 |
| 5,139,620 A | * 8/1992 | Elmore et al. ............. 159/17.1 |
| 5,205,906 A | 4/1993 | Grutsch et al. ............ 159/47.3 |
| 5,814,207 A | 9/1998 | Kenton ........................ 208/184 |

FOREIGN PATENT DOCUMENTS

| | | |
|---|---|---|
| EP | 0 411 500 A | 2/1991 |
| EP | 0 420 756 A | 4/1991 |
| JP | 55 127101 | 10/1980 |
| JP | 3 115244 | 5/1991 |
| JP | 4 74145 | 3/1992 |
| JP | 4 341345 | 11/1992 |

OTHER PUBLICATIONS

Hitachi, "Hitachi Thin–Film Processor", (1991).

* cited by examiner

*Primary Examiner*—Rosalynd Keys
(74) *Attorney, Agent, or Firm*—Morgan, Lewis & Bockius LLP

(57) ABSTRACT

A mixed liquid of two or more components different in boiling temperature from each other and soluble in or compatible with each other is evaporated into a mixed vapor having a similar composition to that of the mixed liquid by using an apparatus having a thin film evaporator (1) having a feed inlet (1*a*) and a delivery outlet (1*b*), while forcedly circulating the non-evaporated portion of the mixed multi-component liquid by withdrawing the non-evaporated mixed liquid portion from the delivery side end portion of the evaporator and returning the mixed liquid portion into the feed side end portion of the evaporator through a circulating line (3), and the resultant mixed multi-component vapor can be used as a mixed material vapor for a gas phase catalytic reaction for producing, for example, a mono and/or a di-alkylether of an aromatic dihydroxy compound.

16 Claims, 3 Drawing Sheets

APPARATUS AND PROCESS FOR GENERATING MIXED MULTI-COMPONENT VAPOR

This is a divisional of copending application Ser. No. 09/178,732, filed Oct. 26, 1998, incorporated herein by reference in its entirety.

BACKGROUND OF THE INVENTION

1. Field of the Invention

The present invention relates to an apparatus and process for generating a mixed multi-component vapor. More particularly, the present invention relates to an apparatus and process for generating a mixed multi-component vapor from a mixed multi-component liquid comprising two or more liquid components different in boiling temperature from each other and soluble in or compatible with each other, by using a thin film evaporator and a forcedly liquid-circulating line connected to the evaporator, the resultant mixed multi-component vapor having a composition very similar to that of the mixed multi-component liquid, and the thermal deterioration of the components being very low.

The present invention includes an apparatus and process for producing a gas phase catalytic reaction product by utilizing the mixed multi-component vapor-generating apparatus and process, respectively.

2. Description of the Related Art

It is well known that a mixed vapor of a plurality of compounds different in boiling temperature from each other can be prepared by separately generating vapors of the compounds from each other, and mixing the resultant vapors in a derived mixing proportion in a mixing vessel.

This conventional mixed vapor-preparing method is disadvantageous in that when at least one compound has a high boiling temperature, and thus must be vaporized at a temperature higher than the high boiling temperature of the compound, the high temperature vaporization applied to the component causes a thermal deterioration of the compound.

Also, it is known that a mixed multi-component vapor can be prepared by preparing a mixture of the components in the state of liquids, and applying a vaporization procedure to the mixed multi-component liquid in a conventional evaporator. When the boiling temperature of the components are different from each other, the composition of the resultant mixed multi-component vapor is different from that of the starting mixed multi-component liquid. The larger the difference in boiling temperature between the components, the larger the difference in composition between the starting mixed multi-component liquid and the resultant mixed multi-component vapor. Usually, the content of a component having a low boiling temperature in the resultant mixed multi-component vapor is higher than it in the starting mixed multi-component liquid.

The conventional apparatus and method for generating the mixed multi-component vapor are disadvantageous in that a mixed multi-component vapor having a desired composition cannot be obtained from a mixed multi-component liquid at a high stability with a high degree of reproducibility under practical conditions.

For example, in a process for producing a monoalkyl ether of a dihydric phenolic compound by a catalytic reaction of a dihydric phenolic compound, for example, catechol, with a lower alkyl alcohol in the gas phase in the presence of a phosphorus-containing catalyst, as disclosed in Japanese Unexamined Patent Publication No. 3-115,244, No. 4-74,149 and No. 4-341,345, a mixed vapor of catechol and the lower alkyl alcohol is fed into a reactor packed with the catalyst to react catechol with the lower alkyl alcohol. In this method, catechol is thermally deteriorated during the mixing and reacting procedures of the mixed vapor to a certain extent, and thus the reaction product contains undesirable by-products, particularly compounds having high boiling temperature. Therefore, there has been a strong demand of removing the above-mentioned disadvantages of the conventional apparatus and method.

For example, there has been attempted a method of preparing a mixed vapor by vaporizing catechol alone and mixing the resultant catechol vapor with a vapor of a lower alkyl alcohol. In this attempt, catechol must be vaporized at a temperature certainly higher than the boiling temperature of catechol and thus was thermally deteriorated to a certain extent. Therefore, this method is not appropriate in practice. In another attempted method, a mixed liquid of catechol and the lower alkyl alcohol was prepared, and then vaporized in an evaporator to provide a mixed vapor. However, in this method, it was found that since a difference in boiling temperature between catechol and the lower alkyl alcohol is large and thus in the resultant mixed vapor, the content of the lower alkyl alcohol is significantly higher than that in the starting mixed liquid. Therefore, in this method, it was very difficult to obtain a mixed vapor having a desired composition from a corresponding mixed liquid by a single evaporation procedure. Namely, this method was unsuccessful in practice.

SUMMARY OF THE INVENTION

An object of the present invention is to provide an apparatus and process for generating a mixed multi-component vapor having a desired composition by evaporating a mixed multi-component liquid having a composition very similar to that of the mixed multi-component vapor, with high reproducibility and high stability, while preventing or restricting undesirable thermal deterioration of the components.

Another object of the present invention is to provide an apparatus and process for generating a mixed multi-component vapor having a desired composition from a mixed multi-component liquid having a composition very similar to that of the mixed vapor, which mixed multi-component vapor can be directly subjected to a reaction, in the gas phase, of the multi-components with each other.

The above-mentioned object can be attained by the apparatus and process of the present invention.

The apparatus of the present invention for generating a mixed multi-component vapor, comprises a thin film evaporator having a feed inlet through which a mixed multi-component liquid comprising two or more liquid components different in boiling temperature from each other and soluble in or compatible with each other is fed into the evaporator and a delivery outlet through which a resultant mixed multi-component vapor is delivered from the evaporator;

a feed line for feeding the mixed multi-component liquid, connected to the feed inlet of the evaporator;

a delivery line for delivering the resultant mixed multi-component vapor, connected to the delivery outlet of the evaporator; and a forcedly liquid-circulating line having a circulation inlet end connected to a delivery side end portion of the evaporator, a circulation outlet end connected to a feed side end portion of the evaporator and a liquid transporting means arranged between the circulation inlet end and the circulation outlet end of the circulating line, whereby a non-evaporated portion of the mixed multi-component liquid is forcedly circulated through the circulation inlet end, the liquid transporting means and the circulation outlet end of the circulating line.

The process of the present invention for generating a mixed multi-component vapor comprises the steps of:

feeding a mixed multi-component liquid comprising two or more liquid components different in boiling temperature from each other and soluble in or compatible with each other into a feed side end portion of a thin film evaporator;

evaporating the mixed multi-component liquid in the evaporator;

and delivering a resultant mixed multi-component vapor from a delivery side end portion of the evaporator, wherein the non-evaporated portion of the mixed multi-component liquid present in the evaporator is forcedly circulated through a circulating line having a circulation inlet end connected to the delivery side end portion of the evaporator, a circulation outlet end connected to the feed side end portion of the evaporator, and forcedly liquid-transporting means located between the circulation inlet end and the circulation outlet end of the circulating line, by withdrawing the non-evaporated portion of the mixed multi-component liquid from the delivery side end portion of the evaporator through the circulation inlet end and returning the withdrawn non-evaporated portion of the mixed multi-component liquid into the feed side end portion of the evaporator through the forcedly liquid-transporting means and the circulation outlet end of the circulating line, thereby to promote the simultaneous evaporation of the two or more liquid components and the generation of a mixed multi-component vapor in which the two or more components are present in substantially the same composition as that of the mixed multi-component liquid.

By utilizing the apparatus of the present invention, a gas phase catalytic reaction product can be produced by an apparatus which comprises:

the mixed multi-component vapor-generating apparatus of the present invention, and a gas phase catalytic reactor connected to the mixed multi-component vapor-generating apparatus through the mixed multi-component-delivery line, and having a delivery line for delivering a resultant reaction product-containing gas fraction from the reactor.

Also, by utilizing the process of the present invention, a gas phase catalytic reaction product can be produced by a process which comprises the steps of:

generating a mixed multi-component vapor in accordance with the process of the present invention, subjecting the mixed multi-component vapor to a gas phase catalytic reaction procedure, and collecting the resultant reaction product-containing gas fraction.

DESCRIPTION OF THE PREFERRED EMBODIMENTS

Figure 1:
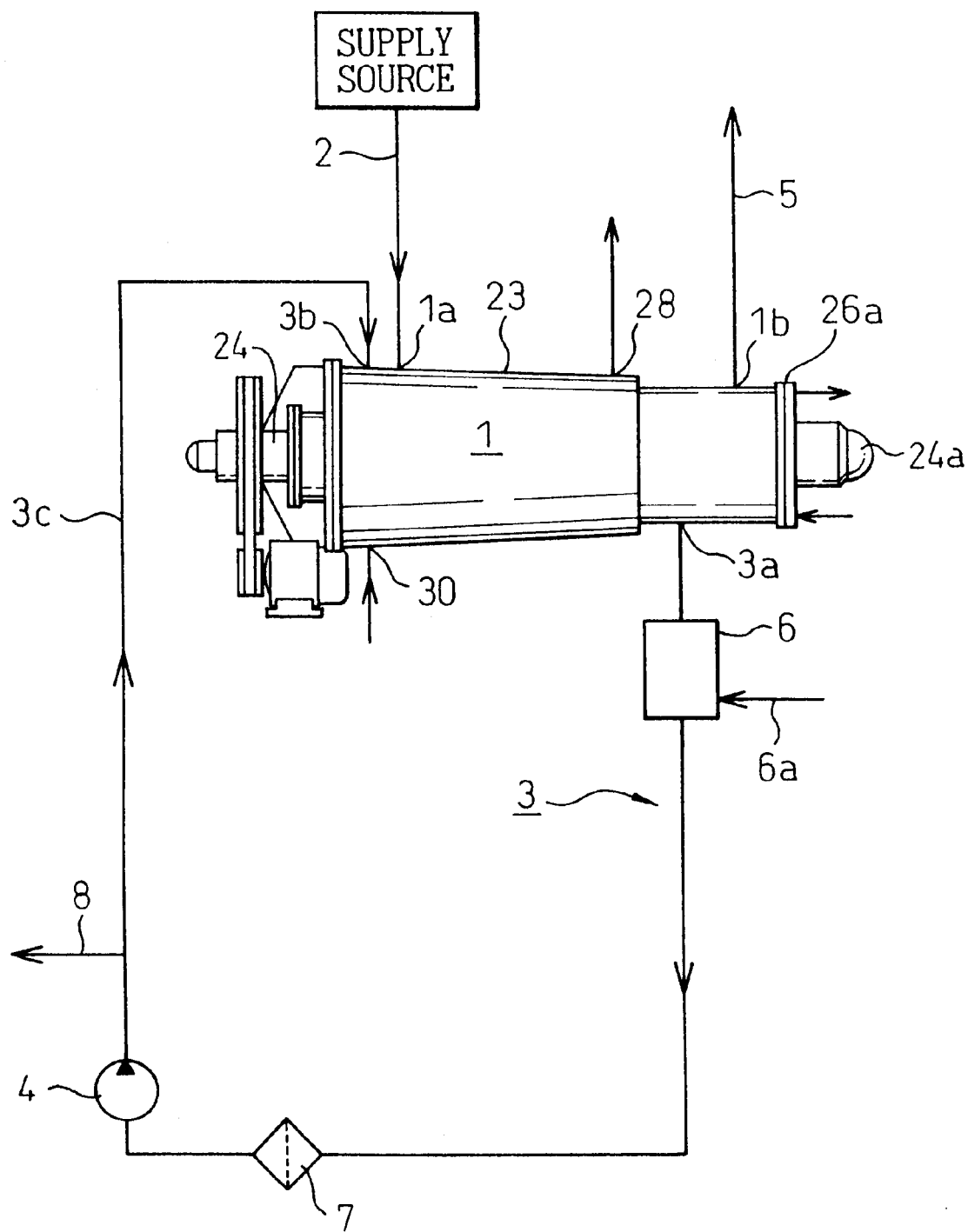
FIG. 1 is an explanatory diagram showing the constitution of an embodiment of the mixed multi-component vapor-generating apparatus of the present invention.

Referring to FIG. 1 showing a constitution an embodiment of the mixed multi-component vapor-generating apparatus of the present invention, a mixed multi-component liquid is fed into a thin film evaporator 1 through a feed line 2 connected to a supply source and a feed inlet 1a located in a feed side end portion of the evaporator 1, heated in the evaporator 1, and a resultant mixed multi-component vapor is delivered from the evaporator 1 through a delivery outlet 1b located in a delivery side end portion of the evaporator 1 and a delivery line 5 to the outside of the evaporator 1.

A non-evaporated portion of the mixed multi-component liquid fed into the evaporator 1 is circulated through forcedly liquid-circulating line 3. In this circulation, the liquid portion is withdrawn into the liquid-circulating line 3 through a circulation inlet end 3a located in the mixed vapor-delivering side end portion of the evaporator 1, by a liquid-transporting means, for example, a liquid pump 4, and then returned into the evaporator 1 through a circulation outlet end 3b located in the mixed liquid-feed side end portion of the evaporator 1.

There is no limitation to the type of the liquid-transporting means 4, as long as the liquid-transporting means 4 can transport the mixed liquid at a desired high temperature. Usually, the liquid-transporting means 4 is selected from plunger type pumps, diaphragm pump, nonseal pumps, and mechanical seal pumps.

Figure 2:
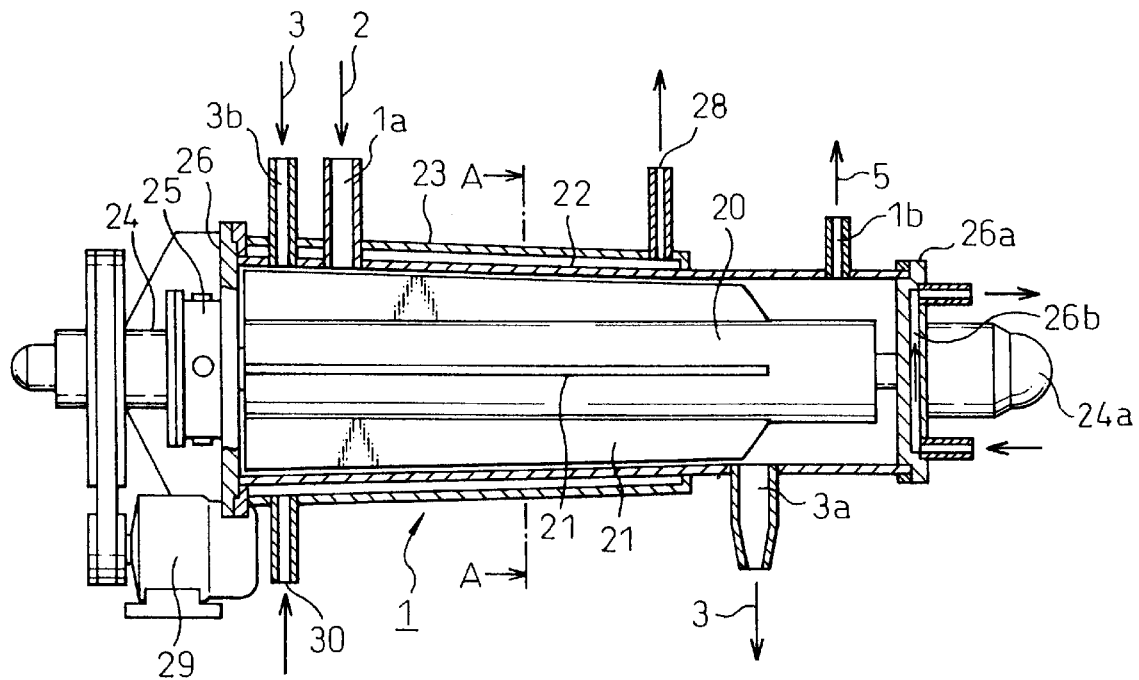
FIG. 2 shows an explanatory cross-sectional front view of an embodiment of a thin film evaporator included in the mixed multi-component vapor-generating apparatus.
Figure 3:
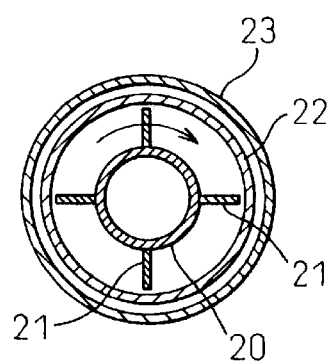
FIG. 3 shows an explanatory cross-sectional side view of the evaporator of FIG. 2, along the line A—A shown in FIG. 2.

In FIGS. 2 and 3, the structure of the thin film evaporator 1 is shown. In FIGS. 2 and 3, a heating body is defined by a peripheral wall 22 and a feed end cover plate 26 and a delivery side end cover plate 26a. The peripheral wall 22 may be in the form of a straight cylinder or of a tapered cylinder as shown in FIG. 2. The peripheral wall 22 of the evaporator 1 has a feed inlet 1a for feeding a mixed multi-component liquid into the evaporator 1 and a delivery outlet 1b for delivery of a resultant mixed multi-component vapor from the evaporator 1. The inlet 1a is arranged in a feed side end portion close to the feed side end cover plate 26 of the evaporator 1 and the delivery outlet 1b is arranged in a delivery side end portion close to the delivery side end cover plate 26a of the evaporator 1. Also, the peripheral wall 22 has a circulation inlet 3a and a circulation outlet 3b of the circulation line 3. The circulation inlet 3a is arranged in the delivery side end portion and the circulation outlet 3b is arranged in the feed side end portion of the evaporator 1. The peripheral wall 22 of the evaporator 1 is surrounded by a heating jacket 23 having an inlet 30 for introducing a heating medium into the heating jacket 23 and an outlet 28 for delivering the heating medium from the heating jacket 23. Also, the delivery side end cover plate 26a has a path 26b through which a heating medium flows to heat the delivery side end portion of the evaporator 1.

A revolving shaft 20 extends through the feed side end cover plate 26, the inside space of the peripheral wall 22 and the delivery side end cover plate 26a along the axis of the evaporator 1. An end portion of the shaft 20 extending to the outside of the feed side end cover plate 26 is supported by a bearing 24 and a shaft-sealing chamber 25 and the shaft 20 is revolved by a motor 29. The opposite end portion of the shaft 20 extending to the outside of the delivery side end cover plate 26a is supported by a bearing 24a.

The revolving shaft 20 has a plurality of agitation wings 21 for agitating the mixed multi-component liquid within the evaporator 1.

Referring to FIGS. 1, 2 and 3, a mixed multi-component liquid comprising two or more component liquids different in boiling temperature from each other and soluble in or compatible with each other is fed into the inside space of the evaporator 1 through a feed line 2 and the feed inlet 1a, is agitated by the revolving agitation wings and is heated by the heating medium flowing through the heating jacket 23 and the flow path 26b to a temperature at which the components in the mixed liquid are evaporated. In this evaporation procedure, a non-evaporated portion of the mixed multi-component liquid in the evaporator 1 is circulated through a circulation line 3. Namely, a non-evaporated portion of the mixed multi-component liquid is introduced into the circulation line 3 through a circulation inlet end 3a by a liquid-transporting means, for example, a liquid pump 4, and returned into the evaporator 1 through a circulation outlet end 3b.

In the evaporator 1, the mixed multi-component liquid is agitated by the revolving wings 21, and a thin film of the mixed liquid is formed on the inside peripheral surface of the peripheral wall 22 and heated by the heating jacket 23, to promote the evaporation of the non-evaporated portion of the mixed multi-component liquid. The circulation of the mixed liquid enables the resultant mixed multi-component vapor to have a similar composition to that of the mixed multi-component liquid. As long as the mixed multi-component liquid can be evaporated in the form of a thin film thereof, there is no limitation to the type, form and dimensions of the evaporator.

In the apparatus of the present invention, the thin film evaporator is preferably selected from horizontal tapered and straight cylinder type thin film evaporators, vertical falling tapered and straight cylinder type thin film-evaporators, vertical rising thin film evaporators, all of which are heat exchangers capable of spreading a thin film of a liquid on an inside peripheral surface thereof. In the tapered cylinder type evaporator, the periphery of the cylinder converges from the feed end to the delivery end thereof.

In the apparatus of the present invention for generating the mixed multi-component vapor, the circulating line 3 optionally has a vessel 6 for storing a portion of the circulating mixed liquid. The storing vessel 6 is arranged between the circulation inlet end 3a and the pump 4 and contributes to enabling the amount of the circulating mixed liquid returned into the evaporator through the circulation outlet end 3b to be constant. The storing vessel 6 may have a returning line 6a connected to a bottom portion of the vessel 6. Through the returning line 6a, a condensed mixed liquid fraction separated from the delivered mixed vapor is returned to the storing vessel 6. The circulating line 3 optionally has a filter 7 located between the storing vessel 6 and the pump 4. The filter 7 can remove solid substances from the circulating mixed liquid.

The circulating line 3 is optionally connected to a discharge line 8 located between the pump 4 and the circulation outlet end 3b, to discharge a portion of the circulating mixed liquid to the outside of the circulating line 3.

The resultant mixed multi-component vapor generated in the evaporator 1 is delivered to the outside of the apparatus through a delivery outlet 1b and a delivery line 5. The delivery line 5 preferably has a heat-insulating means or a heating means, for preventing a local condensation of the mixed vapor passing through the delivery line 5.

Figure 4:
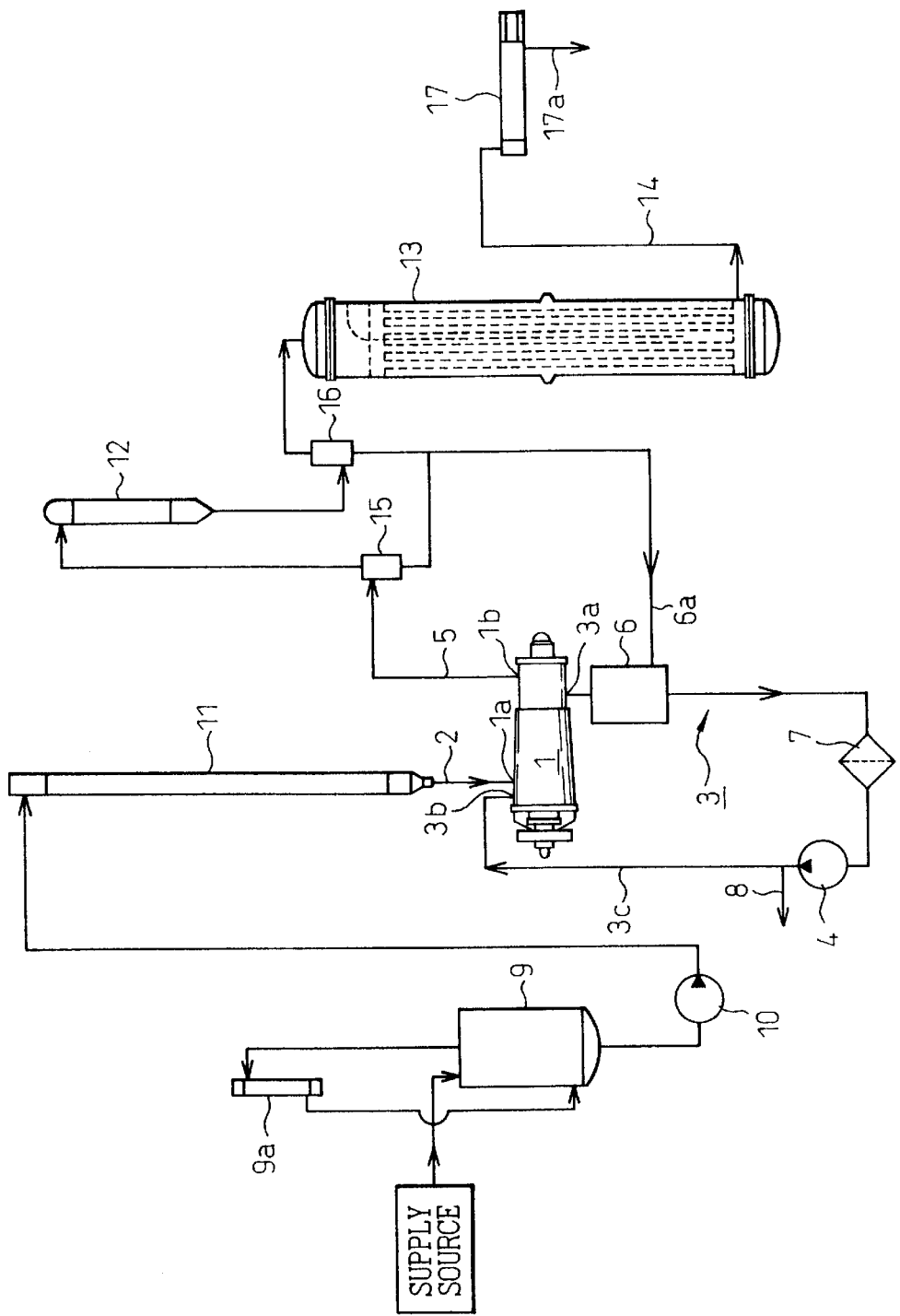
FIG. 4 is an explanatory diagram showing a constitution of an embodiment of an apparatus for producing a gas phase catalytic reaction product, including the mixed multi-component vapor-generating apparatus of the present invention.

Referring to FIG. 4, the feed line 2 is connected a supply source of the mixed multi-component liquid, and optionally has a liquid transporting means, for example, a liquid pump 10, arranged between the supply source and the feed inlet 1a, a mixed liquid-preparation vessel 9 arranged between the supply source and the pump 10, and a preheater 11 arranged between the pump 10 and the feed inlet 1a. When a vapor is generated from the mixed liquid stored in the mixed liquid-preparation vessel 9, the vapor is optionally introduced into a cooler 9a to condense the vapor and the condensed liquid is returned into the mixed liquid-preparation vessel 9. The vessel 9 is used to prepare a mixed multi-component liquid from a plurality of component liquid supplied from the supply source. For the purpose of preparing the mixed liquid, the vessel 9 is optionally equipped with an agitating means (not shown) for uniforming mixing the component liquid, and a heating means (not shown) for dissolving the component liquids in each other.

The preheater 11 may be of a heat-exchanger type using a heating medium.

In the apparatus shown in FIG. 4, the delivery line 5 contacted to the delivery outlet 1b of the evaporator 1 is connected to a gas/liquid separating vessel 15 in which the mixed vapor delivered from the evaporator 1 is separated into a condensed mixed liquid fraction and a non-condensed mixed vapor fraction. The gas/liquid separating vessel 15 is connected to a heater 12 in which the non-condensed mixed vapor fraction delivered from the gas/liquid separating vessel 15 is heated or super heated to a desired temperature. The heater 12 is connected to a gas/liquid separating vessel 16 in which the heated mixed vapor delivered from the heater 12 is separated into a condensed mixed liquid fraction and a non-condensed mixed vapor fraction. The gas/liquid separating vessel 16 is connected to a reactor 13 in which the multi-component vapors in the non-condensed vapor fraction delivered from the gas/liquid separating vessel 16 are reacted with each other, or to a mixed vapor receiver (not shown in FIG. 4).

The reactor 13 may be a gas phase catalytic reactor for catalytically reacting the vapor components with each other.

The reactor 13 has a delivery line 14 for delivering the resultant reaction product from the reactor.

The gas/liquid separating vessels 15 and 16 are connected to a circulating mixed liquid-storing vessel 6 through a returning line 6a through which the condensed mixed liquid fractions separated in the gas/liquid separating vessels 15 and 16 are returned into the storing vessel 6.

The reactor 13 is connected to a cooler 17 through a delivery line 14 through which the reaction product is delivered from the reactor 13. In the cooler 17, the delivered reaction product is cooled to a desired temperature. The cooled reaction product is delivered from the cooler 17 and collected through a delivery line 17a.

In the process of the present invention for generating a mixed multi-component vapor, the mixed multi-component liquid comprising two or more component liquids different in boiling temperature from each other and soluble in or compatible with each other.

The mixed multi-component liquid is preferably fed into the evaporator at a feed temperature of about 50 to 300° C., more preferably 80 to 250° C., still more preferably 100 to 220° C., to prevent or restrict the thermal deterioration of the components, especially those having a high boiling temperature.

The higher boiling point component liquid preferably consists of an organic compound having a boiling temperature of 100 to 350° C., more preferably 120 to 300° C., still more preferably 150 to 290° C., under the ambient atmospheric pressure, substantially non-reactive to other component having a low boiling temperature, and soluble in or compatible with the low boiling temperature components within a temperature range of from 50° C. to 300° C.

The high boiling temperature organic compounds usable for the process of the present invention are preferably selected from those having a low thermal sensibility and a high resistance to thermal deterioration, particularly from those monohydric and dihydric hydroxy aromatic compounds (phenolic compounds) which may be substituted with at least one substitutent selected from, for example, lower alkyl groups preferably having 1 to 6 carbon atoms and halogen atoms.

Particularly, the high boiling temperature organic compounds usable for the process of the present invention are selected from monohydroxy aromatic compounds, for example, phenol and guaiacol; polyhydroxy aromatic compounds, for example, catechol, hydroquinone, and resorcinol; and substituted hydroxy aromatic compounds, for example, 2-methyl catechol, 4-methyl-catechol, 2-methylhydroquinone, 2-chlorocatechol and 4-chlorocatechol.

In the mixed multi-component liquid, the lower boiling point component liquid preferably has a boiling temperature of 50 to 250° C., more preferably 50 to 220° C., still more preferably 60 to 200° C., below the boiling temperature of the higher boiling point organic compound, under the ambient atmospheric pressure. The higher and lower boiling point organic compounds are soluble in or compatible with each other and preferably are non-reactive with each other at a temperature of 50° C. to 300° C.

The lower boiling point organic compounds preferably can dissolve the higher boiling point organic compounds or can be homogeneously mixed with melts of the higher boiling point organic compounds.

The lower boiling point organic compounds are preferably selected from aliphatic alcohols, cycloaliphatic alcohols, aliphatic ethers, aliphatic ketones, aliphatic glycols, and aliphatic carboxylic acid esters, aliphatic hydrocarbons, cycloaliphatic hydrocarbons, and aromatic hydrocarbons, each preferably having a boiling temperature of 50 to 200° C., more preferably 60 to 150° C. The lower boiling point compound may be water.

The lower boiling point aliphatic alcohols include monohydric lower aliphatic alcohols having 1 to 6 carbon atoms, for example, methyl alcohol, ethyl alcohol, n-propyl alcohol, isopropyl alcohol, butyl alcohol, amyl alcohol and hexyl alcohol; and dihydric aliphatic alcohols, for example, ethylene glycol.

The cycloaliphatic alcohols include cyclohexyl alcohol, the ethers include dimethyl ether, diethyl ether, methylethyl ether, methylisopropylether, and methylisobutylether; the ketones include dimethyl ketone and diethyl ketone; and the aliphatic carboxylic acid esters include formic acid esters, acetic acid esters, propionic acid esters and oxalic acid diesters.

In the process of the present invention, the higher boiling point component and the lower boiling point component are preferably mixed in a mixing weight ratio of 0.5:99.5 to 90:10, more preferably 1:99 to 80:20. Still more preferably, the higher boiling point component and the lower boiling point component are mixed in a mixing weight ratio of 20:80 to 80:20, further preferably 30:70 to 70:30.

In the process of the present invention, for example, when 100 parts by weight of a higher boiling point phenolic compound having a boiling temperature of 150 to 300° C., particularly 180 to 290° C., under the ambient atmospheric pressure and 80 to 120 parts by weight a lower boiling point aliphatic alcohol having a boiling temperature of 50 to 200° C., particularly 60 to 150° C., and of 100 to 200° C., particularly 120 to 180° C., below the boiling temperature of the higher boiling point phenolic compound, and compatible with the higher boiling point phenolic compound are mixed with each other, the resultant mixed two-component liquid is useful for generating a mixed two-component vapor having a desired composition with a high efficiency.

In the process of the present invention, the mixed multi-component liquid as mentioned above is fed into a feed side end portion of the thin film evaporator 1; and evaporated in the evaporator, while the non-evaporated portion of the mixed multi-component liquid present in the evaporator is forcedly circulated through a circulating line 3 having a circulation inlet end 3a connected to the delivery side end portion of the evaporator, a circulation outlet end 3b connected to the feed side end portion of the evaporator and a forcedly liquid-transporting means, for example, a liquid pump 4 located between the circulation inlet end and the circulation outlet end of the circulating line, by withdrawing the non-evaporated portion of the mixed multi-component liquid from the delivery side end portion of the evaporator through the circulation inlet end and returning the withdrawn mixed liquid into the feed side end portion of the evaporator through the forcedly liquid-transporting means and the circulation outlet end of the insulating line; and delivering the mixed multi-component vapor from the delivery side end portion of the evaporator. Due to the above-mentioned process, the two or more components are simultaneously evaporated to generate a mixed multi-component vapor in which the two or more components are present in substantially the same composition as that of the mixed multi-component liquid.

In the thin film evaporator, the freshly fed mixed multi-component liquid is evenly mixed with the circulating mixed liquid by the revolving wings, the mixed multi-component liquid is spread in the form of a thin film on the inside peripheral surface of the periphery wall of the evaporator and evaporated.

The revolving wings are revolved at a specific revolution rate determined in consideration of the viscosity of the mixed liquid and the diameter of the wings (a length between the axis of the revolving shaft and the peripheral end of the wing), so that the revolving wings revolve at a peripheral velocity thereof sufficient to form a thin film of the mixed liquid on the inside peripheral surface of the evaporator. In the tapered cylinder type evaporator, the diameter of the wings reduces from the feed end to the delivery end of the evaporator.

For example, when the revolving wings has a radius of 200 to 600 mm, the revolution rate of the wings is preferably 50 to 500 r.p.m., particularly 100 to 300 r.p.m.

In the process of the present invention, the circulating mixed liquid is optionally filtered by a filter 7 for removing solid substances (for example, precipitates) and a portion of the circulating mixed liquid is optionally continuously or intermittently discharged from the circulating line 3 through a discharging line 8, to stabilize the circulation of the mixed liquid over a long time. In the process of the present invention, the feeding flow rate (B) of the mixed liquid and the circulating flow rate (A) of the mixed liquid are preferably in a ratio (B)/(A) of 0.1/1 to 20/1, more preferably 0.5/1 to 15/1, still more preferably 1/1 to 10/1.

When the flow rate ratio (B)/(A) is too high, the residing time of the mixed liquid is increased and thus the thermal deterioration of the higher boiling point component may be increased, and the consumption of heat energy may-be too high. Also, when the ratio (B)/(A) is too low, the resultant mixed vapor may have a composition different from the target composition and/or the composition of the resultant mixed vapor may change with the lapse of time.

In the process of the present invention, the mixed multi-component liquid is spread in the form of a thin film (layer) on the inside peripheral surface of the thin film evaporator and flows from the feed side end portion to the delivery side end portion of the evaporator, while being evenly heated and evaporated. In this procedure, the evaporation temperature of the mixed liquid in the thin film form is determined in response to the composition of the mixed liquid, namely the proportions of the higher boiling point component (or components) and the lower boiling point component (or components), and the boiling temperatures of the individual components. Usually, the evaporation temperature is preferably about 80 to 320° C., more preferably 100 to 300° C., still more preferably 120 to 280° C., to prevent or restrict the thermal deterioration of the higher boiling point components.

In the process of the present invention, the mixed multi-component liquid is evaporated in the thin film evaporator as mentioned above, and the resultant mixed multi-component vapor having a composition similar to the composition of the mixed liquid is delivered from the delivery outlet 1b of the evaporator through the delivery line 5, whereby the resultant mixed vapor having a desired composition can be continuously supplied to a downstream step with a high supply stability. In the downstream step, the mixed vapor is utilized as a material gas for a desired gas phase reaction.

Referring to FIG. 4, the mixed multi-component vapor is delivered from the evaporator 1 through a delivery line 5 and fed into a gas phase reactor 13, optionally through a gas/liquid separating means 15, a heating means 12 and a gas/liquid separating means 16. Preferably, the delivery line is formed from a double pipe having an annular path for passing a heating medium therethrough, or is provided with a heat-insulating means, to prevent partial condensation of the mixed vapor. Also, the delivered mixed vapor is preferably pre-heated or super-heated by a heating means 12 which may be of a heat exchanger type. When a portion of the mixed vapor delivered from the evaporator, and/or a portion of the heated mixed vapor by the heating means 12 is condensed, the condensed liquid fractions are removed by the gas/liquid separating vessels 15 and 16 from the mixed vapor and the heated mixed vapor.

The gas/liquid separating vessels 15 and 16 are connected to the mixed liquid-storing vessel 6 arranged in the circulating line 3. The separated compound liquid fractions are received by the mixed liquid-storing vessel 6.

The apparatus and process of the present invention are advantageously utilized to prepare a material vapor usable for a gas phase catalytic reaction of two or more components with each other, the components being different boiling point from each other and soluble in or compatible with each other.

The gas phase catalytic reaction is usable for the production of alkyl ether of an aromatic dihydroxy compound, particularly an alkyl ether of dihydric phenolic compound from an alkyl alcohol and a dihydric phenolic compound.

The apparatus for producing the gas phase catalytic reaction product comprises:

the mixed multi-component vapor-generating apparatus of the present invention as mentioned above; and a gas phase catalytic reactor connected to the mixed multi-component vapor-generating apparatus through the mixed multi-component-delivering line, and having a delivery line for delivering a resultant reaction product-containing gas fraction from the reactor.

The process for producing the gas phase catalytic reaction product, comprising the steps of:

generating a mixed multi-component vapor in accordance with the process of the present invention, as mentioned above;

subjecting the mixed multi-component vapor to a gas phase catalytic reaction procedure; and collecting the resultant reaction product-containing gas fraction.

In the process for producing the gas phase catalytic reaction product as mentioned above, the mixed multi-component vapor is generated from catechol and a lower alkyl alcohol and, in the reaction step, catechol and the lower alkyl alcohol are reacted with each other in a gas phase in the presence of a catalyst, and the resultant gas fraction containing catechol alkyl ether is collected.

In the mixed catechol-lower alkyl alcohol liquid, preferably catechol and the lower alkyl alcohol are mixed in a mixing weight ratio of 1:99 to 90:10, more preferably 10:90 to 80:20. Still more preferably, the mixing weight ratio of catechol with the lower alkyl alcohol is 30:70 to 70:30, particularly 40:60 to 60:40.

The lower alkyl alcohol is preferably selected from aliphatic alkyl alcohols having 1 to 4 carbon atoms, for example, methyl alcohol, ethyl alcohol, n-propyl alcohol, isopropyl alcohol, n-butyl alcohol, and isobutyl alcohol, particularly methyl alcohol and ethyl alcohol.

The catechol-lower alkyl alcohol mixed liquid is at a temperature of the liquefaction temperature of the mixed liquid or more but not more than the gasification temperature of the mixed liquid, preferably about 100 to 250° C., more preferably 120 to 220° C., to present or restrict the thermal deterioration of catechol.

In the production of an alkyl ether of catechol utilizing the apparatus and process of the present invention, referring to FIGS. 1 to 4, a mixture of a lower alkyl alcohol with catechol is fed into a mixed liquid-preparation vessel 9. When a vapor is generated in the vessel 9, the vapor is fed into a cooler (condenser) 9a and condensed therein. The resultant condensed liquid is returned into the vessel 9. The mixed liquid is fed into a preheater 11 through a pump 10 and is heated to a desired temperature, namely 100 to 250° C. The preheated mixed liquid is fed into the feed side end portion of the evaporator through a feed line 2 and a feed inlet 1a.

The mixed liquid is evaporated in the evaporator 1, while the non-evaporated portion of the mixed multi-component liquid is circulated through the circulating line 3, in the manner as mentioned above.

In the evaporator, the evaporation temperature of the mixed liquid is determined in response to the proportions of the lower alkyl alcohol and catechol. Usually the evaporation temperature is preferably 180 to 280° C., more preferably 200 to 260° C., still more preferably 210 to 240° C., to prevent or restrict the thermal deterioration of catechol.

The resultant mixed vapor having a composition similar to that of the mixed liquid is delivered from the evaporator 1 through a delivery outlet 1b and a delivery line 5.

When a portion of the delivered mixed gas is condensed, the condensed liquid fraction is separated by the gas/liquid separating vessel 15, from the non-condensed mixed vapor, and is returned to the storing vessel 6 through a returning line 6a and mixed with the circulating mixed liquid. The non-condensed mixed vapor is fed into a heating means 12 to heat to a desired temperature, for example, 180° C. or more, and the heated mixed vapor is fed into the gas phase reactor 13. When a portion of the heated mixed gas is condensed, the condensed liquid fraction is removed from the heated mixed vapor by the gas/liquid separating vessel 16, and returned into the storing vessel 6 in the circulating line 3 through the returning line 6a. The returned liquid fraction is incorporated into the circulating mixed liquid in the circulating line 3.

In the reactor 13, the lower alkyl alcohol and catechol in the heated mixed vapor are reacted with each other optionally in the presence of a catalyst, to produce mono or di-lower alkyl ether of catechol.

The resultant gas phase fraction containing a lower alkyl ether of catechol is delivered from the reactor 13 through a delivery line 14. Then, optionally, the delivered reaction product gas containing the target alkyl ether of catechol is fed into a cooler 17, for example, a heat-exchanger type cooler to cool the product gas to a temperature lower than the boiling temperature of the alkyl alcohol, preferably 20° C. or more but more than the boiling temperature of the alkyl alcohol, more preferably 30 to 60° C. The resultant condensed reaction product is collected from the cooler through a collection line 17a.

The collected reaction product is subjected to a distillation procedure to isolate the catechol alkyl ether from the reaction product. Before the distillation procedure, the collected reaction product may be preheated by a heat-exchanger type heater. Then the preheated reaction product is introduced into a distillation column.

In the production of the alkyl ether of catechol, when the catechol-lower alkyl alcohol-mixed liquid is fed at a feed flow rate (B) into the thin film evaporator and circulated at a circulating flow rate (A) through the circulating line, the ratio (B)/(A) of the feed flow rate (B) to the circulating flow rate (A) is preferably 0.5/1 to 20/1, more preferably 1/1 to 15/1, still more preferably 2/1 to 10/1. When the ratio (B)/(A) is too high, the residing time of the mixed liquid in the mixed vapor-generating apparatus may become too long and thus the thermal deterioration of catechol may increase. Also, when the ratio (B)/(A) is too low, the resultant mixed vapor may have a composition different from the target composition, or the desired mixed vapor may not be obtained with a high stability over a long period.

In the production of the alkyl ether of catechol, the catalyst usable in the reactor 13 is not limited to a specific type of catalyst as long as the catalyst can accelerate the gas phase reaction of the lower alkyl alcohol with catechol, as a dehydration reaction catalyst.

The catalyst preferably selected from alkali metal-containing catalyst, for example, hydroxides, carbonates and bicarbonates of alkali metals; p-toluenesulfonic acid and/or aluminum phosphate catalysts; Al—B—P catalysts; Al—B—P-alkaline earth metal catalysts; Al—B—P—Si catalysts; Al—P—Ti—Si catalysts; and catalysts comprising an active component obtained from boric acid and phosphoric acid and carried on a carrier comprising an inert alumina.

For the production of the alkyl ether of catechol, the Al—P catalysts are preferably used. The Al—P catalysts include an Al—P—Ti—Si dehydration reaction catalysts represented by $Al_aP_bTi_cSi_dO_e$ (wherein a, b, c, d and e respectively represent the numbers of Al, P, Ti, Si and O atoms, when a=1, b=1.0 to 1.9, C=0.05 to 0.5, d=0.05 to 0.2 and e=4.1 to 7.0) as disclosed in Japanese Unexamined Patent Publication No. 4-341,345. In the production of the alkyl ether of catechol, the above-mentioned Al—P—Ti—Si catalyst may be added with a catalyst containing 0.004 to 0.015 sulfur atom per atom of aluminum, to provide a composite catalyst.

The gas phase reaction of the lower alkyl alcohol with catechol is preferably carried out in the reactor at a temperature of 200 to 400° C., more preferably 220 to 350° C., still more preferably 230 to 300° C., under an ambient atmospheric pressure or an increased pressure, for example, 1 to 50 kg/cm²G, more preferably 1.5 to 30 kg/cm²G.

The reaction product delivered from the reactor 13 contains, as target products, a catechol monoalkyl ether and catechol dialkyl ether, and as impurities, non-reacted alkyl alcohol, non-reacted catechol, and by-products. In the distillation procedure, the non-reacted alkyl alcohol is removed, as a gas fraction, through a top portion of the distillating column, and the catechol alkyl ethers-containing liquid is delivered, as a liquid fraction from the distillation column. The liquid fraction is subjected to a refining distillation and the distilled catechol alkyl ethers are collected, as a gas fraction, through a top portion of the distilling column. The above-mentioned catechol alkyl ether-producing process is useful for the production of mono alkyl ethers of aromatic dihydroxy compounds, for example, guaiacol and monoethylether of catechol.

EXAMPLES

The present invention will be further illustrated by the following examples, in comparison with the comparative examples.

Example 1

An apparatus as shown in FIGS. 1, 2 and 3 was used to generate a mixed vapor of catechol and methyl alcohol.

In the generation of the mixed catechol-methyl alcohol vapor, a mixed liquid of 54% by weight of catechol and 46% by weight of methyl alcohol was preheated by a preheater to a temperature of 160° C., was fed at a feed rate of 1000 kg/hr into a horizontal thin film evaporator having a heat-transfer area (the inside peripheral surface area of the tapered peripheral wall) of 4 m². The evaporator had a tapered cylinder having an inside diameter of 860 to 750 mm and revolving wings attached to a revolving shaft. The revolving shaft rotated at a rate of 160 r.p.m. In the evaporator, the mixed liquid was heated by passing a heating medium through the heating jacket surrounding the tapered cylinder, and non-evaporated portion of the mixed multi-component liquid was circulated at a circulating rate of 200 kg/hr through a circulating line 3 as shown in FIG. 1.

The mixed liquid in the evaporator was spread in the form of a thin film on the inside peripheral surface of the tapered cylinder by the revolution of the revolving wings, and was heated by the heating jacket.

After the temperature of the mixed liquid withdrawn into the circulating line was set to 225° C. and the level of the mixed liquid received in the storing vessel was kept unchanged, the resultant mixed vapor having a target composition was continuously delivered from the evaporator.

A portion of the circulating mixed liquid was intermittently discharged in an amount of 25 kg once a day from the circulating line, through the discharge line arranged between the liquid pump and the return outlet end of the circulating line.

In Example 1, the mixed vapor-generating procedure could be continuously carried out for 210 days or more, and the deterioration of catechol during the mixed vapor generation was about 0.1% by weight based on the total amount of the fed catechol.

In Table 1, the compositions of the mixed liquid in the feed line 2, circulating line 3 and discharge line 8 from the circulating line and the mixed vapor in the delivery line 5 are shown.

TABLE 1

| Location of mixed liquid and vapor | | | Composition (% by wt.) | | | |
|---|---|---|---|---|---|---|
| (referring to) FIG. 1) | Temperature (° C.) | Flow rate (kg/hr) | catechol | Methyl alcohol | Guaiacol | Deteriorated by-products |
| Mixed liquid in feed line 2 | 160 | 1,000 | 53.9 | 45.9 | 0.25 | — |
| Mixed vapor | 215 | 999 | 53.8 | 45.9 | 0.25 | — |

TABLE 1-continued

| Location of mixed liquid and vapor (referring to) FIG. 1) | Temperature (° C.) | Flow rate (kg/hr) | Composition (% by wt.) | | | Deteriorated by-products |
|---|---|---|---|---|---|---|
| | | | catechol | Methyl alcohol | Guaiacol | |
| in delivery line 5 Mixed liquid circulating through circulating line 3 | 225 | 200 | 50–60 | 0.11–0.38 | 0.25–0.26 | 40–50 |
| Mixed liquid discharged through discharge line 8 | 225 | 25 kg/once a day | " | " | " | " |

Table 1 clearly shows that the composition of the mixed liquid fed through the feed line 2 is quite similar to that of the mixed vapor through the delivery line 5, and this advantageous result can be continuously obtained over a very long period.

Comparative Example 1

A mixed catechol-methyl alcohol vapor was generated by the same procedures as in Example 1 with the following exceptions.

The mixed catechol-methyl alcohol liquid having the same composition as in Example 1 was fed at a feed rate of 1000 kg/hr into the evaporator, while no circulation of the non-evaporated portion of the mixed multi-component liquid was carried out, the amount of the heating medium fed to the heating jacket and the discharge rate of the mixed liquid from the circulating line 3 was changed to 59 kg/hr once a day, and the evaporation was continued for 7 days.

Table 2 shows the average compositions of the mixed liquid in the feed line 2, the circulating line 3 and the discharge line 8 and the mixed vapor in the delivery line 5, in the 7 day procedure.

In Comparative Example 1, the increase in the feed rate of the heating medium caused the amount of the deteriorated by-products from catechol to increase, and the loss of catechol during the mixed vapor-generating procedure reached 11% by weight.

Further, in the comparative example, about 7 days after the start of the mixed vapor-generating procedure, the flow of the mixed liquid became unstable, and scale was deposited in the evaporator, and thus the mixed vapor-generating procedure had to be stopped to remove the scale from the thin film evaporator.

Example 2

An apparatus as shown in FIGS. 1, 2, 3 and 4 was used to generate a mixed vapor of catechol and methyl alcohol and to produce guaiacol from the mixed gas.

In the generation of the mixed catechol-methyl alcohol vapor, a mixed liquid of 54% by weight of catechol and 46% by weight of methyl alcohol was preheated by a preheater to a temperature of 160° C. and was fed at a feed rate of 1000 kg/hr into a horizontal thin film evaporator having a heat-transfer area (the inside peripheral surface area of the tapered peripheral wall) of 4 m². The evaporator had a

TABLE 2

| Location of mixed liquid and vapor (referring to) FIG. 1) | Temperature (° C.) | Flow rate (kg/hr) | Composition (% by wt.) | | | Deteriorated by-products |
|---|---|---|---|---|---|---|
| | | | catechol | Methyl alcohol | Guaiacol | |
| Mixed liquid in feed line 2 | 160 | 1,000 | 53.9 | 45.9 | 0.25 | — |
| Mixed vapor in delivery line 5 | 225 | 941 | 51.0 | 48.8 | 0.25 | — |
| Mixed liquid circulating through circulating line 3 | — | — | — | — | — | — |
| Mixed liquid discharged through discharge line 8 | 240 | 59 kg/once a day | 9.1 | — | Very little | 90.9 | tapered cylinder having an inside diameter of 860 to 750 mm and revolving wings attached to a revolving shaft. The revolving shaft rotated at a rate of 160 r.p.m. In the evaporator, the mixed liquid was heated by passing a heating medium through the heating jacket surrounding the tapered cylinder, and non-evaporated portion of the mixed multi-component liquid was circulated at a circulating rate of 200 kg/hr through a circulating line 3 as shown in FIG. 1.

The mixed liquid in the evaporator was spread in the form of a thin film on the inside peripheral surface of the tapered cylinder by the revolution of the revolving wings, and was heated by the heating jacket.

After the temperature of the mixed liquid withdrawn into the circulating line was set forth at a level of 225° C. and the level of the mixed liquid received in the storing vessel was kept unchanged, the resultant mixed vapor having a target composition was continuously delivered from the evaporator.

A portion of the circulating mixed liquid was intermittently discharged in an amount of 25 kg once a day from the circulating line, through the discharge line arranged between the liquid pump and the return outlet end of the circulating line.

The mixed catechol-methyl alcohol vapor delivered from the evaporator was super heated to a temperature of 230° C. by a heat exchanger using a heating medium, mixed with a mixed gas separately prepared from a boron compound as a component of an etherification (dehydration reaction) catalyst and methyl alcohol, and then fed, as a material vapor, into a gas phase reactor packed with a phosphorus-containing etherification catalyst (as disclosed in Japanese Unexamined Patent Publication No. 4-341,345, Example 1). In the reactor, catechol catalytically reacted with methyl alcohol at a reaction temperature of 270° C. under a reaction pressure of 0.35 kg/cm$^2$G, to produce guaiacol. The resultant guaiacol-containing gas was delivered from the reactor, and cooled and condensed by a cooler. The condensed liquid was collected from the cooler and stored in a storage tank.

The production of guaiacol of Example 2 could be continued for 210 days or more and the deterioration of catechol during the mixed vapor generation was about 0.1% by weight based on the total amount of the fed catechol.

In Table 3, the compositions of the mixed liquid in the feed line 2, circulating line 3 and discharge line 8 from the circulating line, the mixed vapor in the delivery line 5 and the reaction product vapor in the delivery line 14 from the reactor 13 are shown.

The compositions shown in Table 3 are average values during the 100 day procedure.

TABLE 3

| Location of mixed liquid and vapor (referring to) FIG. 1) | Temperature (° C.) | Flow rate (kg/hr) | Composition (% by wt.) | | | | |
|---|---|---|---|---|---|---|---|
| | | | catechol | Methyl alcohol | Guaiacol | Deteriorated by-products | Others |
| Mixed liquid in feed line 2 | 160 | 1,000 | 53.9 | 45.9 | 0.25 | — | — |
| Mixed vapor in delivery line 5 | 215 | 999 | 53.8 | 45.9 | 0.25 | — | — |
| Mixed liquid circulating through circulating line 3 | 225 | 200 | 50–60 | 0.11–0.68 | 0.25–0.26 | 40–50 | — |
| Mixed liquid discharged through discharge line 8 | 225 | 25 kg/once a day | " | " | " | " | — |
| Reaction product vapor delivered through delivery line 14 | 270 | 999 | 26.9 | 35.7 | 28.6 | 0.7 | 8.1 |

Comparative Example 2

A mixed catechol-methyl alcohol vapor was generated and guaiacol was produced from the mixed vapor by the same procedures as in Example 2 with the following exceptions.

The mixed catechol-methyl alcohol liquid having the same composition as in Example 1 was fed at a feed rate of 1000 kg/hr into the evaporator, while no circulation. of the non-evaporated portion of the mixed multi-component liquid was carried out, the amount of the heating medium fed to the heating jacket and the discharge rate of the mixed liquid from the circulating line 3 was changed to 59 kg/hr once a day, and the. guaiacol-production was continued for 7 days.

Table 4 shows the average compositions of the mixed liquid in the feed line 2, the circulating line 3 and the discharge line 8, the mixed vapor in the delivery line 5, and the reaction product vapor in the delivery line 14. from the reactor 13 in the 7 day procedure.

TABLE 4

| Location of mixed liquid and vapor (referring to) FIG. 1) | Temperature (° C.) | Flow rate (kg/hr) | Composition (% by wt.) | | | | |
|---|---|---|---|---|---|---|---|
| | | | catechol | Methyl alcohol | Guaiacol | Deteriorated by-products | Others |
| Mixed liquid in feed line 2 | 160 | 1,000 | 53.9 | 45.9 | 0.25 | — | — |
| Mixed vapor in delivery line 5 | 225 | 941 | 51.0 | 48.8 | 0.25 | — | — |
| Mixed liquid circulating through circulating line 3 | — | — | — | — | — | — | — |
| Mixed liquid discharged through discharge line 8 | 240 | 59 kg/once a day | 9.1 | — | Very little | 90.9 | — |
| Reaction product vapor in delivery line 14 | 270 | 941 | 23.7 | 38.5 | 29.0 | 0.8 | 8.0 |

In Comparative Example 2, the increase in the feed rate of the heating medium caused the amount of the deteriorated by-products from catechol to increase, and the loss of catechol during the mixed vapor-generating procedure reached 11% by weight.

Further, in the comparative example, about 7 days after the start of the mixed vapor-generating procedure the flow of the mixed liquid became unstable, and scale was deposited in the evaporator, and thus the mixed vapor-generating procedure had to be stopped to remove the scale from the thin film evaporator.

In the production of the alkyl ether of dihydric phenolic compound utilizing the apparatus and process of the present invention, a mixed vapor of alkyl alcohol and the dihydric phenolic compound having a similar composition to that of the mixed liquid thereof can be obtained with a high stability while preventing or restricting the thermal deterioration of the dihydric phenolic compound, and thus the target alkyl ether can be produced with a high efficiency and with a high stability over a long period.

What we claim is:

1. A process for generating a mixed multi-component vapor comprising the steps of:

feeding a mixed multi-component liquid comprising two or more liquid components different in boiling temperature from each other and soluble in or compatible with each other into a feed side end portion of a thin film evaporator;

evaporating the mixed multi-component liquid in the evaporator;

and delivering a resultant mixed multi-component vapor from a delivery side end portion opposite to the feed side end portion of the evaporator;

wherein a non-evaporated portion of the mixed multi-component liquid present in the evaporator is forcedly circulated through a circulating line having a circulation inlet end connected to the delivery side end portion of the evaporator, a circulation outlet end connected to the feed side end portion of the evaporator, and forcedly liquid-transporting means located between the circulation inlet end and the circulation outlet end of the circulating line, by withdrawing the non-evaporated portion of the mixed multi-component liquid from the delivery side end portion of the evaporator through the circulation inlet end and returning the withdrawn non-evaporated portion of the mixed multi-component liquid into the feed side end portion of the evaporator through the forcedly liquid-transporting means and the circulation outlet end of the circulating line, thereby to promote the simultaneous evaporation of the two or more liquid components and the generation of a mixed multi-component vapor in which the two or more components are present in substantially the same composition as that of the mixed multi-component liquid.

2. The mixed multi-component vapor-generating process as claimed in claim 1, wherein the mixed multi-component liquid present in the thin film evaporator is heated to evaporate the mixed multi-component liquid.

3. The mixed multi-component vapor-generating process as claimed in claim 1, wherein the feeding flow rate (B) of the mixed multi-component liquid and the circulating flow rate (A) of the mixed multi-component liquid are in a ratio (B)/(A) of 0.1/1 to 20/1.

4. The mixed multi-component vapor-generating process as claimed in claim 1, wherein the mixed multi-component liquid comprises a higher boiling point organic compound having a boiling temperature of 100 to 350° C. and a lower boiling point organic compound having a boiling temperature of 50 to 250° C. below the boiling temperature of the higher boiling point organic compound, the higher and lower boiling point organic compounds being soluble in or compatible with each other and non-reactive with each other at a temperature of 50 to 300° C.

5. The mixed multi-component vapor-generating process as claimed in claim 4, wherein the higher boiling point organic compound is selected from the group consisting of aromatic compounds having one or more hydroxyl groups.

6. The mixed multi-component vapor-generating process as claimed in claim 5, wherein the aromatic compounds having one or more hydroxyl group are selected from the group consisting of phenol, guaiacol, catechol, hydroquinone, resorcinol, 2-methyl catechol, 4-methyl catechol, 2-methyl hydroquinone, 2-chlorocatechol and 4-chlorocatechol.

7. The mixed multi-component vapor-generating process as claimed in claim 4, wherein the lower boiling point organic compound is selected from the group consisting of aliphatic alcohols, cycloaliphatic alcohols, aliphatic ethers, aliphatic ketones, aliphatic glycols, aliphatic carboxylic acid esters, aliphatic hydrocarbons, cycloaliphatic hydrocarbons and aromatic hydrocarbons, each having a boiling temperature of 50 to 200° C., and water.

8. The mixed multi-component vapor-generating process as claimed in claim 1, wherein the resultant mixed multi-component vapor is subjected to a catalytic gas phase reaction in which the two or more vapor components are catalytically reacted with each other, and the resultant reaction product-containing gas fraction is collected.

9. The mixed multi-component vapor-generating process as claimed in claim 1, wherein the mixed multi-component liquid comprises catechol and a lower alkyl alcohol having 1 to 4 carbon atoms, and evaporated to form a catechol-lower alkyl alcohol mixed vapor.

10. The mixed multi-component vapor-generating process as claimed in claim 9, wherein in the mixed multi-component liquid, catechol and the lower alkyl alcohol are mixed in a mixing weight ratio of 1:99 to 90:10.

11. The mixed multi-component vapor-generating process as claimed in claim 9, wherein the catechol-lower alkyl alcohol-mixed liquid is evaporated at a temperature of 100 to 250° C.

12. The mixed multi-component vapor-generating process as claimed in claim 9, wherein the catechol-lower alkyl alcohol-mixed liquid is fed at a flow rate (B) into the evaporator and circulated at a flow rate (A) through the circulating line, and the ratio (B)/(A) of the feed flow rate (B) to the circulating flow rate (A) is 0.5/1 to 20/1.

13. The mixed multi-component vapor-generating process as claimed in claim 9, wherein the resultant catechol-lower alkyl alcohol-mixed vapor is subjected to a gas phase catalytic reaction, and the resultant catechol alkyl ether-containing gas fraction is collected.

14. The mixed multi-component vapor-generating process as claimed in claim 13, wherein the collected catechol alkyl ether-containing gas fraction is subjected to a distillation procedure to isolate the catechol alkyl ether.

15. A process for producing a gas phase catalytic reaction product, comprising the steps of:

generating a mixed multi-component vapor in accordance with the process as claimed in claim 1, subjecting the mixed multi-component vapor to a gas phase catalytic reaction procedure, and collecting the resultant reaction product-containing gas fraction.

16. The process as claimed in claim 15, wherein the mixed multi-component vapor is generated from catechol and a lower alkyl alcohol and, in the reaction step, catechol and the lower alkyl alcohol are reacted with each other in a gas phase in the presence of a catalyst, and the resultant gas fraction containing catechol alkyl ether is collected.

* * * * *